United States Patent
Wang (10) Patent No.: US 9,259,293 B2
(45) Date of Patent: Feb. 16, 2016

(54) BONE CARVING TOOL FOR CREATING CONVEX RIDGE FOR INNER BORDER OF INITIAL HOLE FOR PLACEMENT OF IMPLANT HOLE

(75) Inventor: Je-Won Wang, Yuseong-gu (KR)

(73) Assignee: INNOBIOSURG, Daejeon (KR)

( * ) Notice: Subject to any disclaimer, the term of this patent is extended or adjusted under 35 U.S.C. 154(b) by 74 days.

(21) Appl. No.: 14/006,891

(22) PCT Filed: Mar. 21, 2012

(86) PCT No.: PCT/KR2012/002001
§ 371 (c)(1),
(2), (4) Date: Oct. 31, 2013

(87) PCT Pub. No.: WO2012/128542
PCT Pub. Date: Sep. 27, 2012

(65) Prior Publication Data
US 2014/0099598 A1    Apr. 10, 2014

(30) Foreign Application Priority Data
Mar. 24, 2011 (KR) .................. 10-2011-0026615

(51) Int. Cl.
A61C 3/00 (2006.01)
A61C 3/02 (2006.01)
A61C 8/00 (2006.01)
A61B 17/16 (2006.01)

(52) U.S. Cl.
CPC ............... *A61C 3/02* (2013.01); *A61B 17/1604* (2013.01); *A61C 3/00* (2013.01); *A61C 8/0089* (2013.01)

(58) Field of Classification Search
CPC .......... A61C 8/0089; A61C 3/00; A61C 3/02; A61B 17/1604
USPC ......................................... 433/165, 144, 173
See application file for complete search history.

(56) References Cited

U.S. PATENT DOCUMENTS

| 749,624 | A | * | 1/1904 | McCullough | 433/165 |
| 2,715,772 | A | * | 8/1955 | Fritz | 433/165 |
| 6,257,889 | B1 | * | 7/2001 | Boston | 433/165 |
| 6,575,748 | B1 | * | 6/2003 | Filhol | 433/102 |
| 6,854,972 | B1 | * | 2/2005 | Elian | 433/173 |
| 7,547,210 | B1 | * | 6/2009 | Valen | 433/165 |
| 2005/0003327 | A1 | | 1/2005 | Elian et al. | |
| 2007/0259314 | A1 | * | 11/2007 | Danger et al. | 433/165 |

(Continued)

FOREIGN PATENT DOCUMENTS

EP 2 119 403 A1 * 11/2009
KR 10 2005 0081979 A 8/2005

(Continued)

*Primary Examiner* — Ralph Lewis
(74) *Attorney, Agent, or Firm* — Sughrue Mion, PLLC

(57) ABSTRACT

The present invention relates to a bone carving tool for creating a convex ridge for the inner border of the initial hole for placement of an implant hole, and comprises: a bone carving unit with tapering diameters ranging from 2 to 7 mm, which has a plurality of triangular-shaped projections disposed on the lateral sides thereof forming a triangular prism-shape; and a supporting portion for supporting the bone carving unit connected to the bone carving unit at a lower aspect thereof, wherein the diameter of the bone carving unit gradually narrows towards the upper aspects thereof and the uppermost aspects of the plurality of triangular-shaped projections and the triangular prism-shape coalesce to a single point.

1 Claim, 9 Drawing Sheets (2A)

(2B)

(2C)

(56) References Cited

U.S. PATENT DOCUMENTS

2011/0306981 A1 12/2011 Wang
2012/0244497 A1* 9/2012 Huwais .................... 433/165

FOREIGN PATENT DOCUMENTS

| KR | 10 0962166 B1 | 6/2010 |
| WO | WO 2010/128771 A2 * | 11/2010 |

* cited by examiner

BONE CARVING TOOL FOR CREATING CONVEX RIDGE FOR INNER BORDER OF INITIAL HOLE FOR PLACEMENT OF IMPLANT HOLE

TECHNICAL FIELD

The present invention relates to a bone carving tool for creating a convex ridge for the inner border of the initial hole for placement of an implant hole capable of creating a convex ridge for the inner border of the hole so that internal or external bending may be possible without break of the cortical bone by using a structure which allows easy contraction of the inner bone to absorb the condensing pressure which is generated at the inner bone of the hole at the time of bone extension of the alveolar bone as an operation tool which is used at the implant operation.

BACKGROUND ART

Generally, implant originally refers to a substitute which restores the tissue of a human body when the tissue is lost, but in dental medicine, implant refers to transplantation of artificial teeth.

Implant is an advanced operation which allows restoration of the original function of teeth by fixing artificial teeth after implanting artificial dental root made of titanium without rejection in the body to substitute the dental root of the lost teeth, and in the case of a general dental prosthesis or artificial teeth, as time goes by, the surrounding teeth and bones are damaged, but in the case of implant, the surrounding dental tissues are not damaged and the implant is not decayed while having the similar function and shape as those of natural teeth, and thus implant may be used relatively for a long time.

Generally, when implant operation is performed at the alveolar bone, the width of the alveolar bone needs to be secured, and when implant operation is not possible due to the narrow width of the alveolar bone of a patient, the cortical bone is incised and the alveolar bone is split by using a chisel, and then the split crack is extended by using the spreader or osteotome for implant operation.

However, in such an operation, the cortical bone is significantly incised, and thus the damaged range gets large and the bone grafts may be separated. Further, the bone graft materials and blocking membrane need to be necessarily used, which is inconvenient and economically burdensome, and thus there have been many studies on solving such a problem.

For example, Korean Patent Publication No. 10-2007-0119628 discloses a new platform including an implant 1 for teeth and related parts. Here, the implant 1 and the related parts have a reduced diameter, and thus are appropriate for a predetermined use for healing the narrow width area of the bone. It discloses the technology of readjusting or optimizing a predetermined feature and geometric form of the implant 1 for teeth and the related parts in order to obtain narrow, but strong and reliable implant 1 for teeth and related parts.

Korean Patent Publication No. 10-0821074 discloses a bone tissue extender for maintaining the extended state of the incised bone tissue of the region where the implant operation is performed. The bone tissue extender for implant operation includes a support 20 which is horizontally formed at the body 10, where a hole 24 having a spiral groove 22 at the inner circumference is formed, a fix structure which is vertically formed to the body 10, where an insertion space is formed at the center, an operation structure 40 which moves forwards or backwards at the internal side of the hole 24 as the spiral groove 42, which is spirally coupled with the spiral groove 22 of the inner circumference of the hole 24, is formed at the outer circumference, and the screw driver 60 is inserted into the spiral groove 42, and a movement extension structure 50 which is located on the same line as that of the fix structure 30 in the insertion space 32 of the center of the fix structure 30, where the operation axis 52 linked with the operation structure 40 is formed at the backside.

Korean Patent Publication No. 10-0630304 discloses a reamer for implant operation including an incision unit for forming a hole for implant placement, and a connection unit which is extended to the lower part of the incision unit and has a diameter smaller than that of the incision unit. The incision unit includes a projected side which is formed by lifting one surface including an outer circumference of the upper front surface of the incision unit, a depressed side which has a reverse slope to the clockwise direction where one side of the upper front surface of the incision is fallen, a discharge path from a certain part between the projected side and the depressed side to the region close to the bottom of the incision unit.

Korean Patent Publication No. 10-0884211 discloses piezotome for vertical approach operation maxillary sinus including piezo body whose one end is inserted into and fixed at the hand piece of the piezo main device, a piezo pole which is extended to the other end of the piezo body and has a linear or bended structure, and a piezo tip where a plurality of cutting blades are formed at regular intervals to continue the cutting at a part of the piezo pole.

A plurality of cutting blades 14 of the piezo tip 13 are formed in a hemisphere shape. Further, the a hole 15 for water supply, which penetrates the piezo body 11, the piezo pole 12, and the piezo tip 13, are formed at the inner center of the piezotome. Further, the stopper 16 for restricting the inserting distance according to the thickness of the remaining bone is integrally projected at the outer circumference of the piezo pole.

DISCLOSURE

Technical Problem

Figure 7:
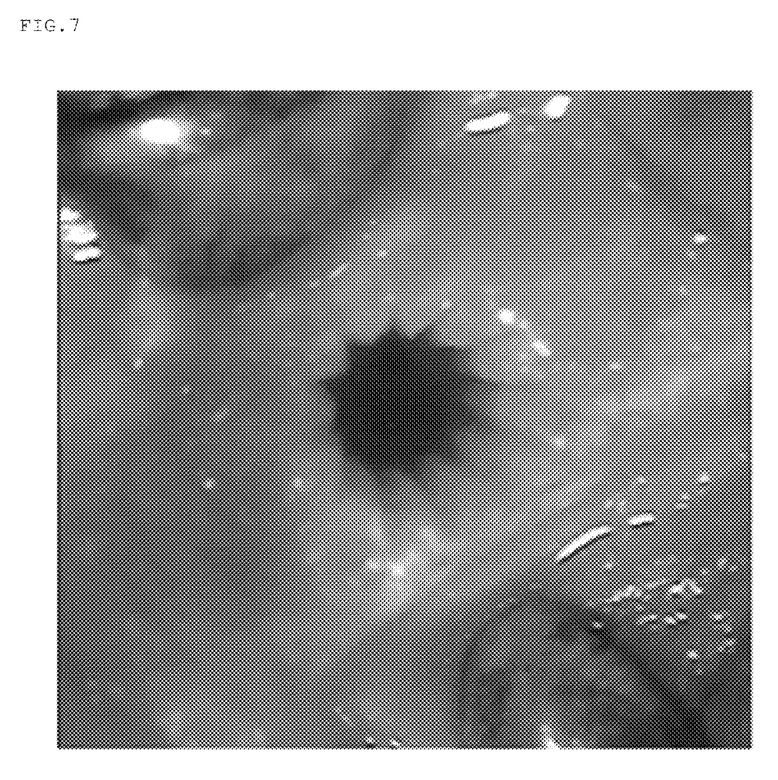
FIG. 7 is a photograph of implant operation which is performed using a bone carving tool which creates a convex ridge for the inner border of the initial hole of the present invention.
Figure 8:
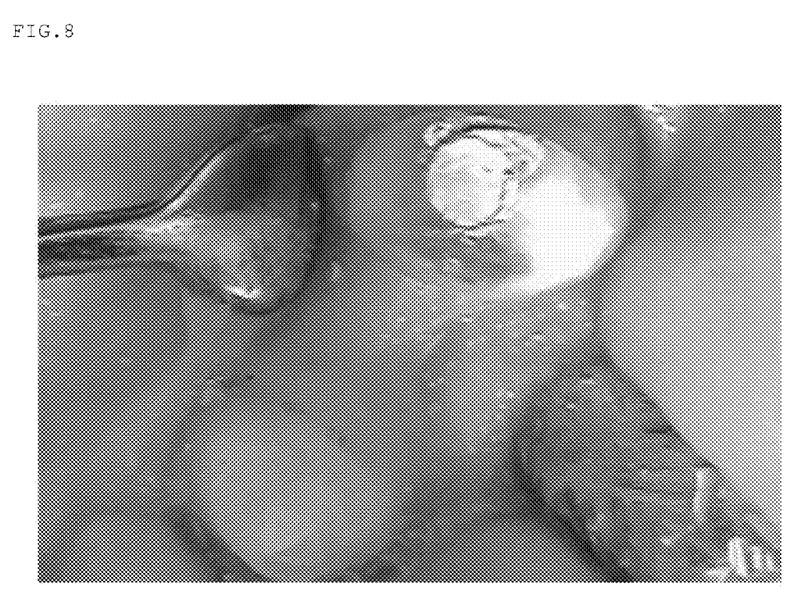
FIG. 8 is a photograph before implant operation which is performed using a bone carving tool which creates a convex ridge for the inner border of the cortical bone hole of the present invention.

When the cortical bone is bent and extended without break, the condensing pressure is absorbed by the projection formed at the internal side and the external side may be appropriately extended as in FIG. 7. Referring to FIG. 8, at the time of extension, the internal condensing pressure is generated, tensile force is generated at the external side, and the condensing pressure is added in an extended direction, i.e., at the external bone, and thus the break occurs from the external bone to the internal bone side.

Hence, an object of the present invention is to provide a bone carving tool for creating a convex ridge for the inner border of the hole capable of absorbing condensing pressure which is generated by forming a structure which allows easy contraction of the internal bone when forming a bone which is needed in bone extension of the alveolar bone.

Technical Solution

In order to solve the above problem, a bone carving tool for creating a convex ridge for the inner border of the initial hole for placement of an implant hole is provided, and according to the bone carving tool, an initial hole is formed by drilling at the time of bone extension for dental implant placement, then the projected from is formed at the inner border of the initial hole without break of the cortical bone, and then extension is made by striking by osteotome.

Advantageous Effects

According to the present invention, the convex ridge and the diameter which fit the bony substance of the alveolar bone of the patient may be selected for operation, and thus effective use may be possible and the operation time may be reduced. Furthermore, at the time of operation, when the alveolar bone is extended, by forming the necessary bone, the structure capable of absorbing the condensing pressure generated at the inner border of the initial hole may be formed to prevent break of the cortical bone from the external side to the inner surface. Hence, the severe damage according to excessive bone incision which is needed at the existing bone extension, the economic burden according to the use of graft materials and the blocking membrane, and the operation failure such as break of the bone grafts may be prevented, and thus the operation effect during and after implant operation may be enhanced.

BEST MODE

After teeth are removed, in order to form a hole for placement in the narrow alveolar bone for implant operation, first drilling is performed by using a first implant drilling tool to form an initial hole (refer to FIG. 4A).

The bone carving unit supporting portion is grabbed by one hand, and a hammer is grabbed by another hand. Then the lower end of the supporting portion is struck by the hammer and force (vertical pressure) is applied to form a projection in a form of the bone carving unit body 32 on the inner border of the second initial hole (see FIG. 4B). Furthermore, the osteotome of an extendable size is inserted and struck so that the bone is externally pushed (extending the alveolar bone) from the internal surface of the hole and a third extension is made in a regular width (see FIG. 4C). Then the implant operation is performed by fixing the implant at the center of the extended hole.

DETAILED DESCRIPTION OF EXEMPLARY EMBODIMENTS

The present invention relates to a bone carving tool for creating a convex ridge for the inner border of the initial hole for placement of an implant hole, and comprises: a bone carving unit with tapering diameters ranging from 2 to 7 mm, which has a plurality of triangular-shaped projections disposed on the lateral sides thereof forming a triangular prism-shape; and a supporting portion for supporting the bone carving unit connected to the bone carving unit at a lower aspect thereof, wherein the diameter of the bone carving unit gradually narrows towards the upper aspects thereof and the uppermost aspects of the plurality of triangular-shaped projections and the triangular prism-shape coalesce to a single point.

According to the present invention, the lower part of the bone carving supporting portion of the bone carving tool may be directly stuck or may be coupled with the existing holder (existing strike-type bone carving tool) to be used. According to the prior art, the cortical bone is incised by drilling without using the bone carving tool, and the bone grafts are pushed for the green stick fracture by using an extender (spreader or osteotome), and thus many bone incisions need to occur and bone grafts may be broken and separated, and graft materials and blocking membrane need to be always used. Hence, the operation is difficult and there is an economic burden, and operation time and recovery time is lengthened.

When implant operation is firstly performed in a narrow place in the alveolar bone, a small hole is formed by drilling, the inner surface of the hole is secondly formed by striking the bone carving tool into the inner surface of the initial hole, and the third extension is performed by striking by the osteotome.

The present invention is a kind of a strike-type bone carving tool, and a plurality of triangular prism shape or triangular projections on the lateral sides, and the triangular prism shape and triangular projection types are preferably symmetrical, and the number according to the diameter is as follows.

Φ2.0 to Φ2.9: between 4 and 9
Φ3.0 to Φ3.9: between 5 and 11
Φ4.0 to Φ4.9: between 5 and 13
Φ5.0 to Φ5.9: between 6 and 15
Φ6.0 to Φ7.0: between 7 and 18

Appropriate selection may be used according to the bone condition, and the appropriate lower diameter (maximum diameter) of the bone carving tool is 2 to 7 mm.

That is, if more triangular projections are used for hard bone and less triangular projections are used for soft bone, the bone carving may be easily performed.

Hereinafter, the present invention will be described in detail below.

Exemplary Embodiment

After teeth are removed, in order to form a hole for placement in the narrow alveolar bone for implant operation, first drilling is performed by using a first implant drilling tool to form an initial hole (refer to FIG. 4A).

The bone carving unit supporting portion is grabbed by one hand, and a hammer is grabbed by another hand. Then the lower end of the supporting portion is struck by the hammer and force (vertical pressure) is applied to form a projection in a form of the bone carving unit body 32 on the inner border of the second initial hole (see FIG. 4B). Furthermore, the osteotome of an extendable size is inserted and struck so that the bone is externally pushed (extending the alveolar bone) from the internal surface of the hole and a third extension is made in a regular width (see FIG. 4C). Then the implant operation is performed by fixing the implant at the center of the extended hole.

Hereinafter, the present invention will be described in detail with reference to the attached drawings.

Figure 1:
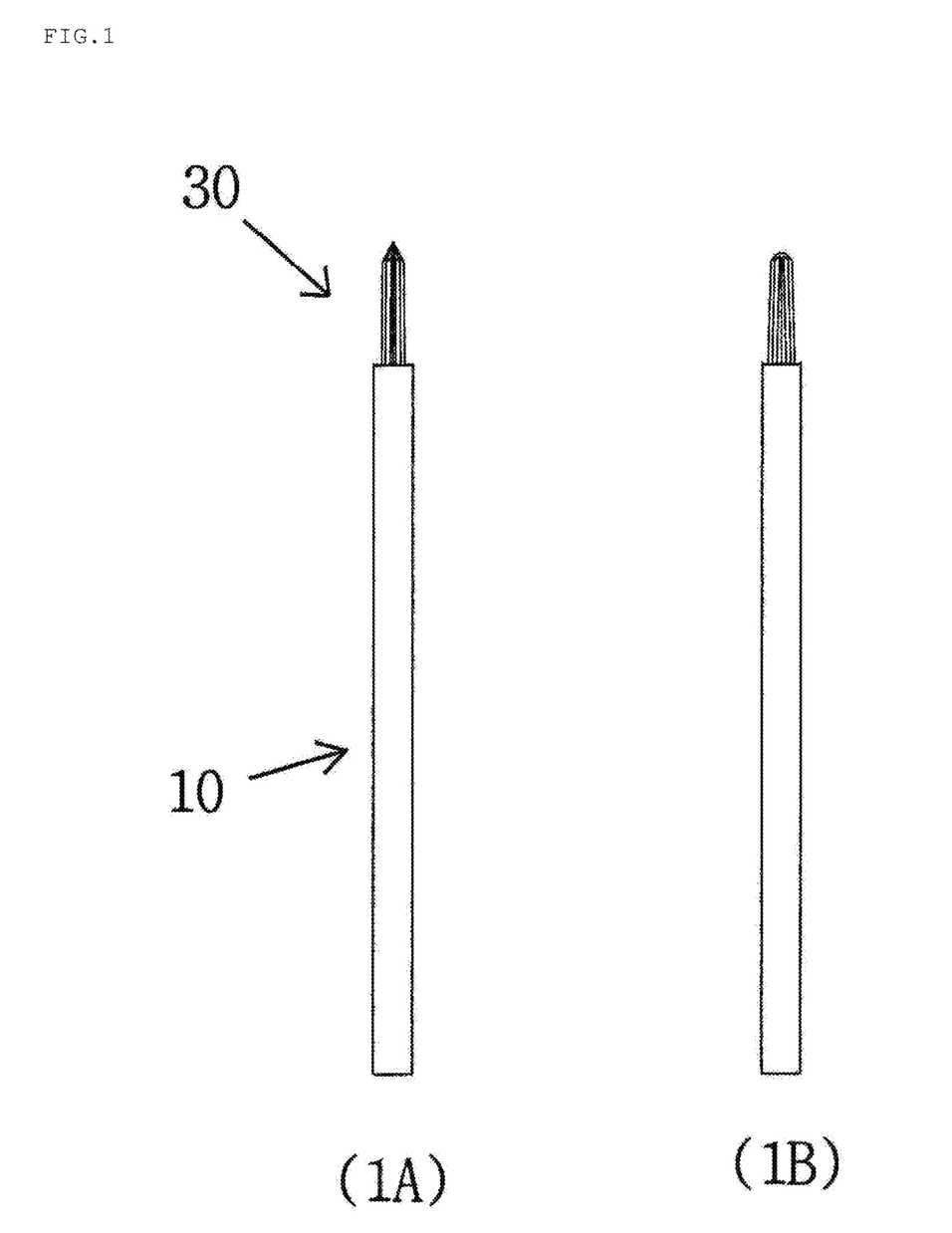
FIG. 1 schematically illustrates a bone carving tool for creating a convex ridge for the inner border of the initial hole for placement of an implant hole of the present invention.
Figure 2:
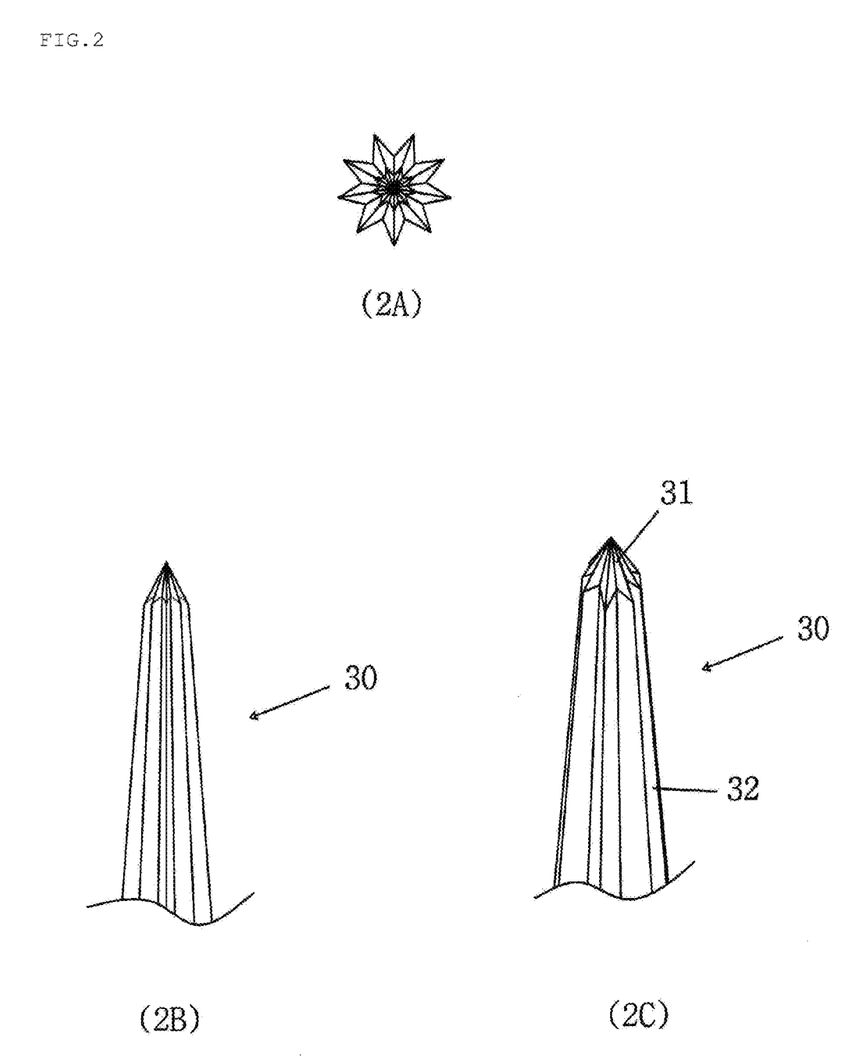
FIG. 2 specifically illustrates a bone carving unit of the present invention.
Figure 3:
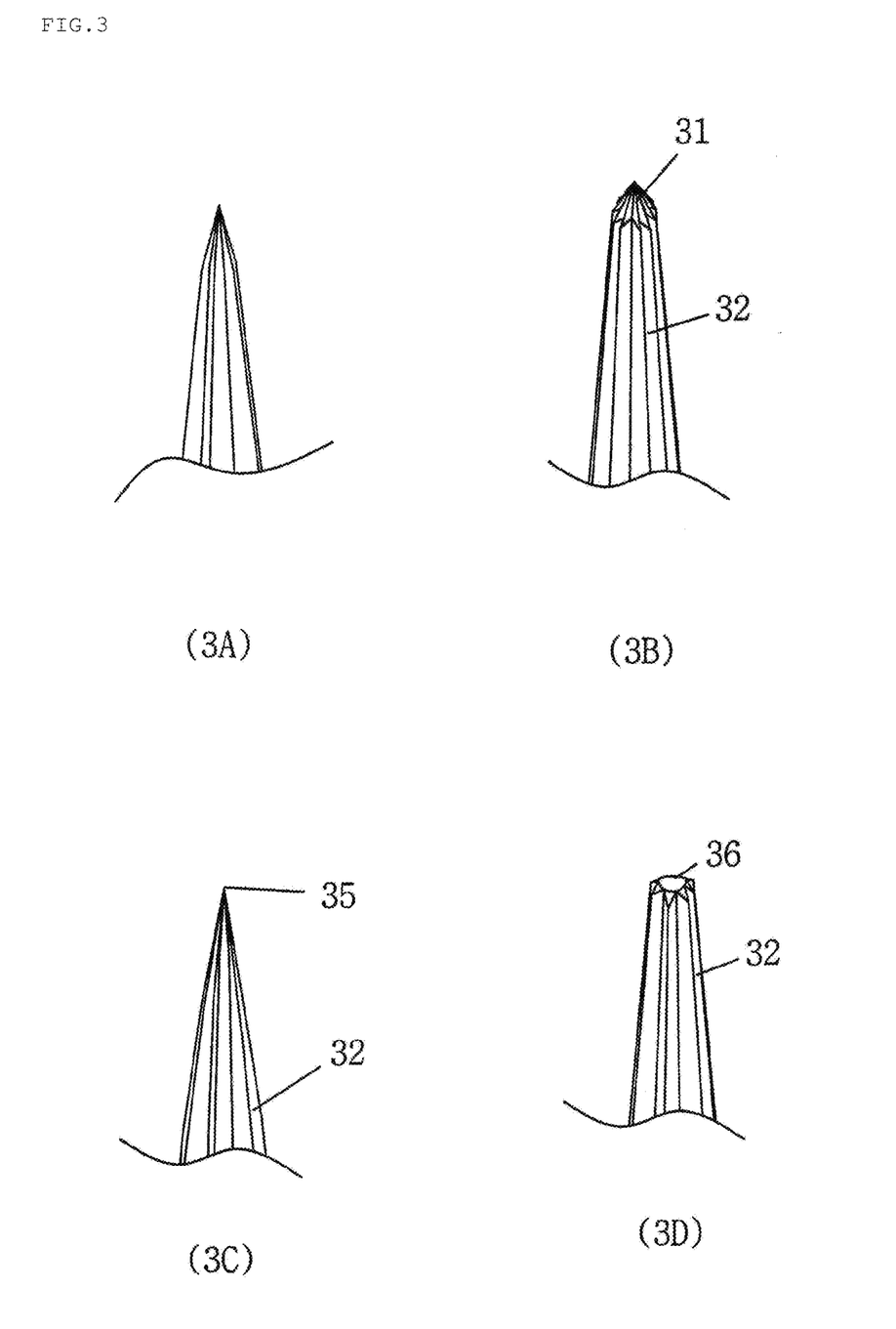
FIG. 3 illustrates various upper states of a bone carving unit of the present invention.
Figure 4:
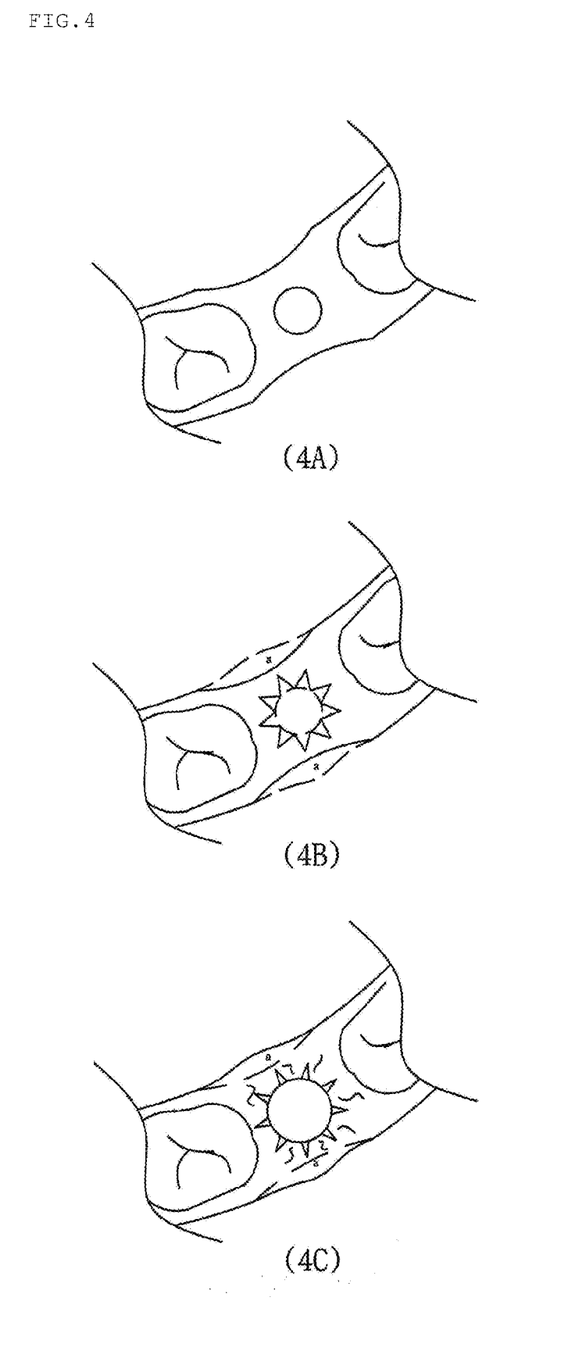
FIG. 4 illustrates a state of using a bone carving tool for creating a convex ridge for the inner border of the initial hole for placement of an implant hole, and extending the bone.
Figure 5:
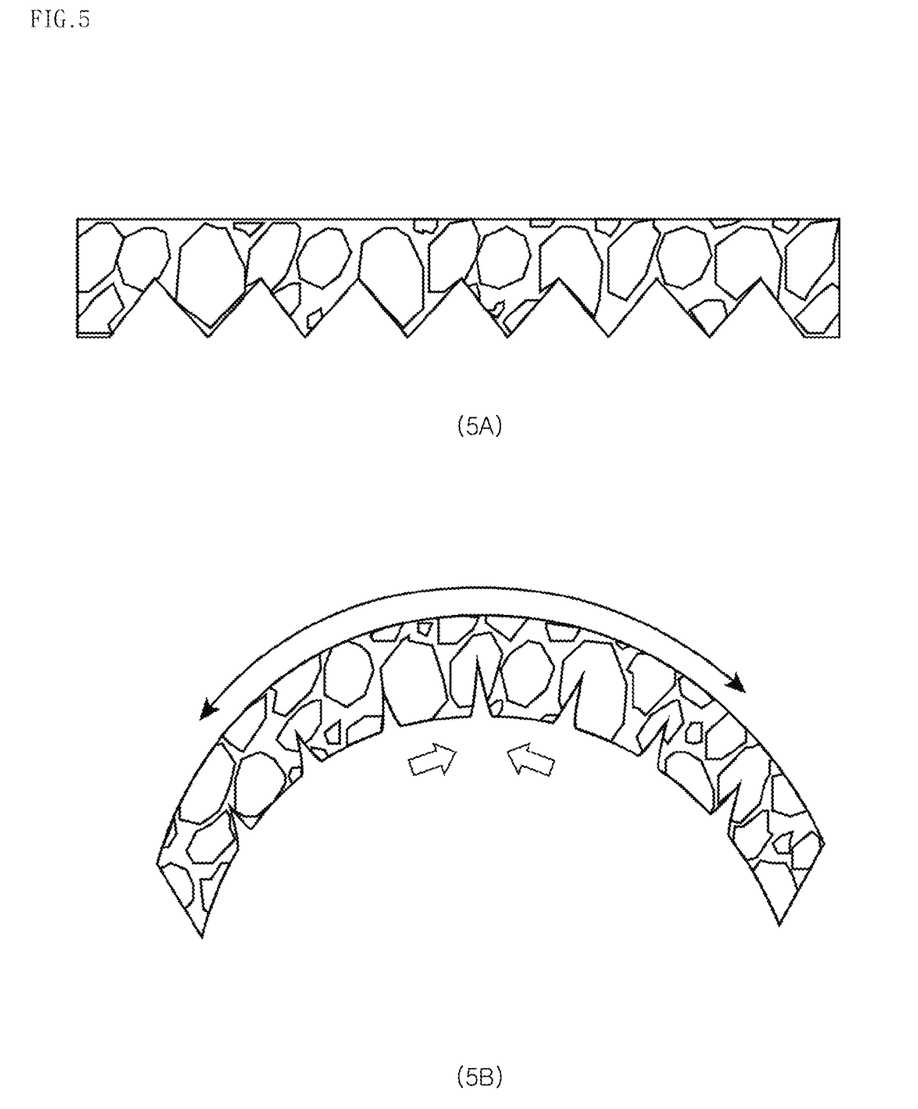
FIG. 5 illustrates a state where a convex ridge is created for the inner border to absorb condensing pressure, and the external border is appropriately extended.
Figure 6:
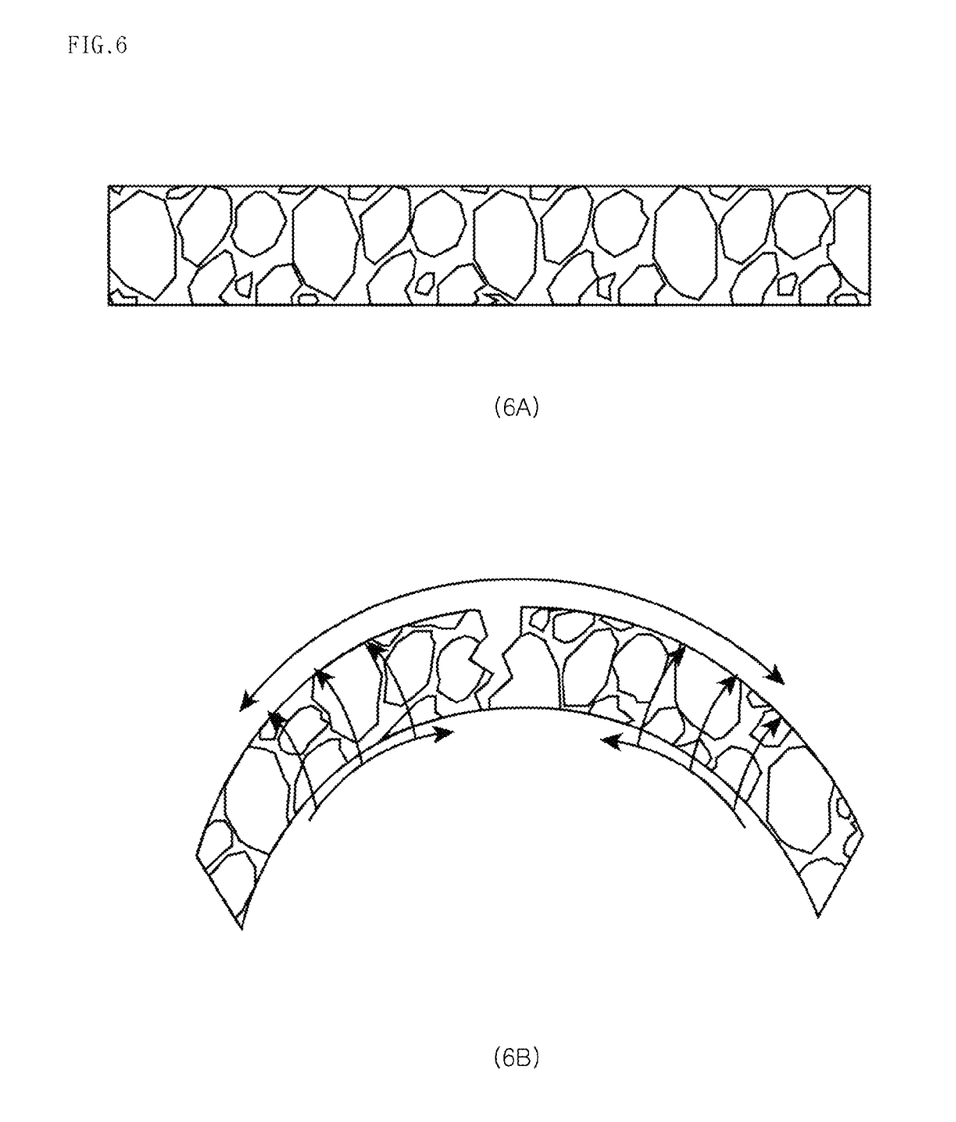
FIG. 6 illustrates a state where, when the bone is extended for implant placement, an internal convex space is reduced to generate the condensing pressure, the tension is generated at the external border, and the condensing pressure is delivered from the internal bone to the external bone to destroy the external bone.
Figure 9:
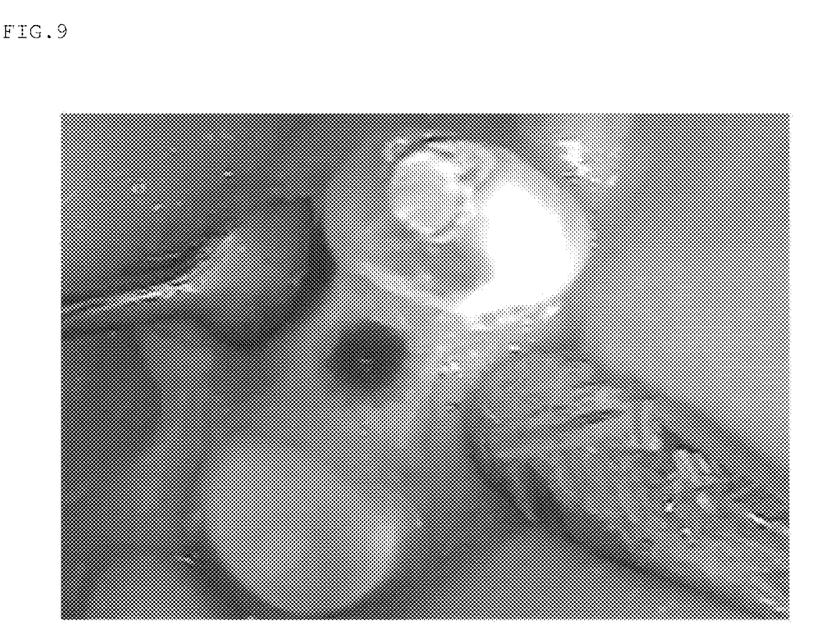
FIG. 9 is a photograph of a state where the initial hole is drilled at the inner border, is formed by the bone carving tool to receive the convex ridge, and is then extended by the osteotome without break of the cortical bone.

FIG. 1 schematically illustrates a bone carving tool for creating a convex ridge for the inner border of the initial hole for placement of an implant hole of the present invention, FIG. 2 specifically illustrates a bone carving unit of the present invention, FIG. 3 illustrates various upper states of a bone carving unit of the present invention, FIG. 4 illustrates a state of using a bone carving tool for creating a convex ridge for the inner border of the initial hole for placement of an implant hole, and extending the bone, FIG. 5 illustrates a state where a convex ridge is created for the inner border to absorb condensing pressure, and the external border is appropriately extended, FIG. 6 illustrates a state where, when the bone is extended for implant placement, an internal convex space is reduced to generate the condensing pressure, the tension is generated at the external border, and the condensing pressure is delivered from the internal bone to the external bone to destroy the external bone, FIG. 7 is a photograph of implant operation which is performed using a bone carving tool which creates a convex ridge for the inner border of the initial hole of the present invention, FIG. 8 is a photograph before implant operation which is performed using a bone carving tool which creates a convex ridge for the inner border of the cortical bone hole of the present invention, and FIG. 9 is a photograph of a state where the initial hole is drilled at the inner border, is formed by the bone carving tool to receive the convex ridge, and is then extended by the osteotome without break of the cortical bone. Furthermore, the bone carving unit support 10, the bone carving unit 30, the upper end of the bone carving unit 31, 35, and 36, and the bone carving unit body 32 are shown.

The structure is described below.

FIG. 1A shows a bone carving tool which creates a convex ridge for the inner border of the initial hole for placement of an implant hole. The bone carving tool includes a bone carving unit 30 and a bone carving unit supporting portion 10 which is attached on the lower part of the bone carving unit 30.

The diameter of the bone carving unit 30 is between 2 to 7 mm, and the bone carving unit includes a plurality of projections of a triangular prism shape or triangular projection shape, and includes a bone carving unit body 32 wherein the diameter narrows towards the upper part and the projections also get smaller, and an upper end 31 of the bone carving unit which is formed by concentration of projections of a triangular prism shape or triangular projection shape.

FIG. 1B illustrates a bone carving unit which creates a convex ridge on the inner border of the cortical bone hole in the bone carving tool which creates a convex ridge for the inner border of the initial hole for placement of an implant hole.

The bone carving unit 30 and the bone carving unit supporting portion 10 which is attached on the lower part of the bone carving unit 30 are included.

The diameter of the bone carving unit 30 is between 2 to 7 mm, and the bone carving unit includes a plurality of projections of a triangular prism shape or triangular projection shape, and includes a bone carving unit body 32 wherein the diameter narrows towards the upper part and the projections also get smaller, and an upper end 36 of a cut form in which projections of a triangular prism shape or triangular projection shape are not concentrated into a single point.

As illustrated in FIG. 2, the bone carving tool, which creates a convex ridge for the inner border of the initial hole for placement of an implant hole, includes a bone carving unit 30, a bone carving unit upper end 31, a bone carving unit body 32, and a bone carving unit supporting portion 12. The bone carving unit 30 includes the bone carving unit body 32 with tapering diameters ranging from 2 to 7 mm, which has a plurality of triangular-shaped projections disposed on the lateral sides thereof forming a triangular prism-shape, and a bone carving unit body 32, wherein the diameter of the bone carving unit gradually narrows towards the upper aspects thereof and the uppermost aspects 31 of the plurality of triangular-shaped projections and the triangular prism-shape coalesce to a single point.

FIG. 3 illustrates another example of a bone carving unit, and illustrates the bone carving unit body 32 of the bone carving unit 32 and various forms of the bone carving unit upper ends 31, 35, and 36.

FIG. 3B illustrates a plurality of triangular-shaped projections and the triangular prism-shape of the bone carving unit body 32.

FIG. 3C illustrates a bone carving unit body 32 including a plurality of projections of a triangular-shape and a triangular prism-shape which are externally formed on the lateral sides, wherein the diameter narrows towards the upper part.

The end of the bone carving unit body 32 includes the bone carving unit upper end 35 which is sharply formed as a plurality of triangular prism-shape or triangular-shape projections are coalesced.

FIG. 3D shows a bone carving unit body 32 including a plurality of projections of a triangular-shape and a triangular prism-shape which are externally formed on both sides, wherein the diameter narrows towards the upper part. The end of the bone carving unit body 32 indicates the upper part of the bone carving part which enables the cortical bone, which has been formed in a cut shape, to be bent without break.

FIG. 4 illustrates a state of using a bone carving tool for creating a convex ridge for the inner border of the initial hole for placement of an implant hole, and extending the bone. When implant operation is firstly performed in a narrow place in the alveolar bone, a small hole is formed by drilling (see FIG. 4A), the inner surface of the hole is secondly formed by striking the bone carving tool into the inner surface of the initial hole (FIG. 4B), and the third extension is performed by striking by the osteotome (FIG. 4C). Then the narrow part of the alveolar bone is bent by "a" amount so that the implant operation may be easily performed.

The use and operation state will be described below.

After teeth are removed, in order to form a hole for placement at the narrow alveolar bone for implant operation, a hole is firstly formed by drilling using the first implant drilling tool (see FIG. 4A).

The bone carving unit supporting portion is grabbed by one hand, and a hammer is grabbed by another hand. Then the lower end of the supporting portion is struck by the hammer and force (vertical pressure) is applied to form a projection in a form of the bone carving unit body 32 on the inner border of the second initial hole (see FIG. 4B). Furthermore, the osteotome of an extendable size is inserted and struck so that the bone is externally pushed (extending the alveolar bone) from the internal surface of the hole and a third extension is made in a regular width (see FIG. 4C). Then the implant operation is performed by fixing the implant at the center of the extended hole.

In other words, by striking (vertical pressure) the bone carving tool which creates the convex ridge for the inner border of the initial hole for placement of implant hole, as in FIG. 9, the bone is formed in a convex form on the initial hole border and the bone may be bendable without break of the cortical bone.

INDUSTRIAL APPLICABILITY

As described above, the convex ridge and the diameter which fit the bony substance of the alveolar bone of the patient may be selected for operation, and thus effective use may be possible and the operation time may be reduced. Furthermore, at the time of operation, when the alveolar bone is extended, by forming the necessary bone, the structure capable of absorbing the condensing pressure generated at the inner border of the initial hole may be formed to prevent break of the cortical bone from the external side to the inner surface. Hence, the severe damage according to excessive bone incision which is needed at the existing bone extension, the economic burden according to the use of graft materials and the blocking membrane, and the operation failure such as break of the bone grafts may be prevented, and thus the operation effect during and after implant operation may be enhanced.

The invention claimed is:

1. A bone carving tool for creating a convex ridge for an inner border of an initial hole for placement of an implant hole, the tool comprising:

a bone carving unit; and
a supporting portion for supporting the bone carving unit and connected to a lower part of the bone carving unit,
wherein the bone carving unit has a diameter ranging from 2 mm to 7 mm and includes a bone carving unit body having a plurality of triangular shaped projections formed in a radial shape, and an upper end portion having a plurality of triangular shaped projections formed in the radial shape corresponding to the plurality of triangular shaped projections of the bone carving unit body,
wherein a size of each of the plurality of triangular shaped projections of the bone carving unit body becomes smaller towards an upper end of the bone carving unit as the diameter of the bone carving unit becomes smaller towards the upper end of the bone carving unit,
wherein a tilt angle of each of the plurality of triangular shaped projections of the upper end portion is different from a tilt angle of each corresponding triangular shaped projection of the plurality of triangular shaped projections of the bone carving unit body so that the plurality of triangular shaped projections of the upper end portion coalesce to a single point at the upper end of the bone carving unit,
wherein each of the triangular shaped projections of the bone carving unit body has two flat sides extending from the lower part of the bone carving unit toward the upper end portion of the bone carving unit, and
where the number of the triangular shaped projections of the bone carving unit body is five or more, and the number of the triangular shaped projections of the upper end portion is five or more.

\* \* \* \* \*